United States Patent [19]

McShane

[11] 4,075,219
[45] Feb. 21, 1978

[54] EPIMERIZATION PROCESS

[75] Inventor: Lawrence J. McShane, Indianapolis, Ind.

[73] Assignee: Eli Lilly and Company, Indianapolis, Ind.

[21] Appl. No.: 783,123

[22] Filed: Mar. 31, 1977

[51] Int. Cl.² .......................................... C07D 513/04
[52] U.S. Cl. ........................ 260/306.7 C; 260/239 A; 260/343 G; 260/448.2 B; 260/534 M; 560/35; 560/39; 560/22
[58] Field of Search ................................ 260/306.7 C

[56] References Cited

U.S. PATENT DOCUMENTS 2,450,784  10/1948  Duffin et al. .................. 260/306.7 C
3,966,752  1/1976  Asinger et al. ............... 260/306.7 C Primary Examiner—R. J. Gallagher
Attorney, Agent, or Firm—William B. Scanlon; Arthur R. Whale

[57] ABSTRACT

A process for preparing the compound represented by the formula

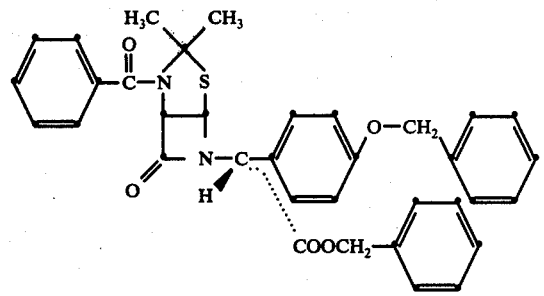

wherein the indicated carbon has the D-configuration which comprises dissolution of the compound in the L-configuration or as a mixture of the D and L-configurations in aqueous pyridine from which the compound having the D-configuration selectively crystallizes.

4 Claims, No Drawings

EPIMERIZATION PROCESS

BACKGROUND OF THE INVENTION

This invention relates to a process for preparing 2-benzoyl-3,3-dimethyl-7-oxo-α-[4-(benzyloxy)phenyl]-4-thia-2,6-diazabicyclo[3.2.0]heptane-6-acetic acid, benzyl ester which is represented by the following structural formula

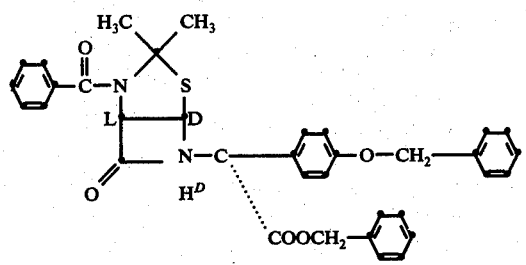

wherein the 3-centers of asymmetry have the indicated configuration. This invention is concerned with a process for epimerizing the asymmetric center attached to the N of the azetidinone ring of the above compound.

The bicyclic compound represented by the above formula is referred to herein for convenience as a thiazolidine-azetidinone. The compound in the D-configuration is useful as an intermediate in the process for the preparation of the antibiotic substance nocardicin which is described in co-pending application Ser. No. 739,161 filed Nov. 5, 1976. As described therein, the thiazolidine-azetidinone having the D-configuration is a preferred isomer of the intermediate in the preparation of nocardicin. In the described process, the preparation of the thiazolidine-azetidinone is carried out as illustrated in the reaction schemes below. L-cysteine is heated with acetone and the product, 2,2-dimethyl-thiazolidine-4-carboxylic acid (1), is acylated with benzoyl chloride in the presence of a hydrogen halide acceptor to provide the 2,2-dimethyl-3-benzoylthiazolidine-4-carboxylic acid (2). The 3-benzoyl thiazolidine-4-carboxylic acid is then converted to the amide (3) formed with the benzyl ester of 4-benzyloxyphenylglycine. The formation of the amide is conveniently carried out by first converting the thiazolidine carboxylic acid to the active ester formed with 1-hydroxybenzotriazole. The formation of the active ester is carried out by condensing the acid with the hydroxybenzotriazole in the presence of a condensing agent such as dicyclohexylcarbodiimide. The active ester of the thiazolidine carboxylic acid is then used to acylate the α-amino group of the phenylglycine to form the amide (3).

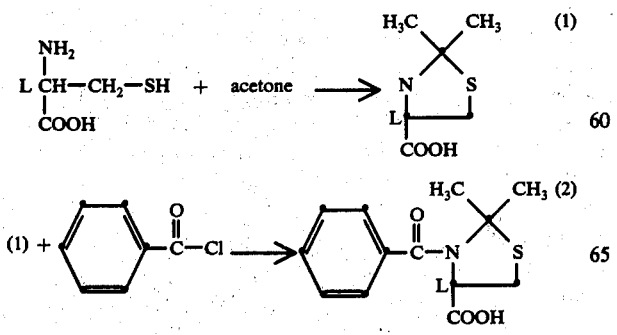

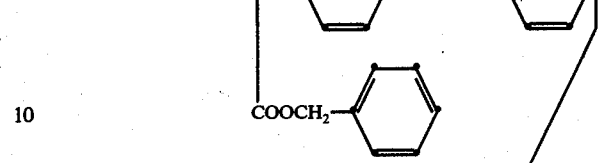

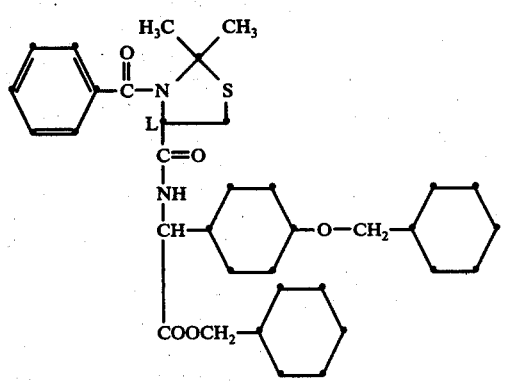

The thiazolidine amide (3) is converted to the cyclic thiazolidine-azetidinone as shown in the following reaction scheme.

(3) + benzoyl peroxide ⟶

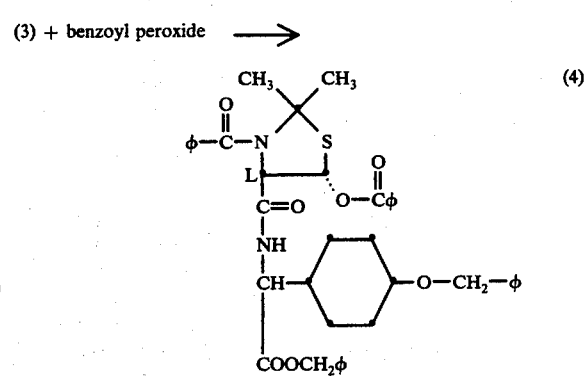

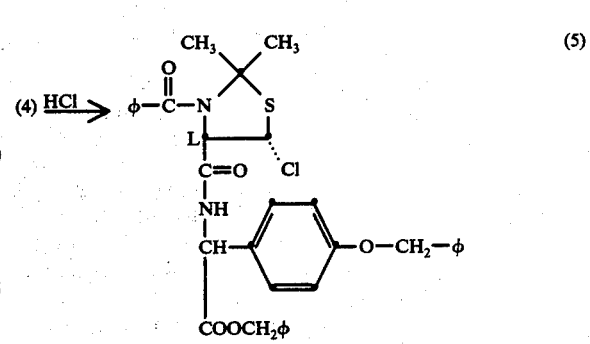

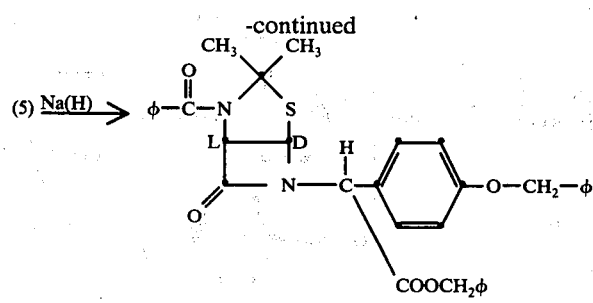

As shown above, the thiazolidine amide (3) is first converted to the 5α-benzoate derivative (4) by reacting (3) with benzoyl peroxide. The reaction is carried out by heating the amide in an inert solvent with benzoyl peroxide. Suitable solvents include the hydrocarbon solvents such as benzene and toluene, or the chlorinated hydrocarbon solvents such as methylene chloride and chloroform. An excess of benzoyl peroxide is employed and preferably between about a 2 and 4 molar excess.

The 5α-benzoate (4), which can be purified and separated from unreacted starting material by chromatography over silica gel, is then reacted with hydrogen chloride in an inert solvent at a temperature between about −20° and about 5° C. to form the corresponding 5α-chloro thiazolidine amide represented by the above Formula (3). The reaction is conveniently carried out in a chlorinated hydrocarbon solvent such as methylene chloride or chloroform, and the progress of the reaction can be followed by thin layer chromatography.

The 5α-chloro compound (5) on treatment under anhydrous conditions with a strong base such as sodium hydride or 1,5-diazabicyclo[5.4.0]undec-5-ene (DBU) undergoes cyclization to form the bicyclic thiazolidine-azetidinone.

The cyclization is carried out at a temperature between about 0° and 30° C. in an inert solvent. Suitable solvents include those previously mentioned in connection with the foregoing reactions, for example, the halogenated hydrocarbon solvents such as chloroform, DMF and methylene chloride, and trichloroethane. The product of the cyclization is best purified by chromatography over silica gel. Gradient elution employing a gradient of benzene to benzeneethyl acetate (7:3, v:v) is a suitable chromatographic system.

The base catalyzed cyclization of the 5α-chlorothiazolidine carboxamide results in epimerization of the asymmetric center in the phenylglycine portion of the amide. Accordingly, when D-phenylglycine is employed as starting material in the preparation of the bicyclic thiazolidine-azetidinone, the base catalyzed cyclization results in epimerization leading to a mixture of the D- and L-thiazolidine-azetidinones. Although the D- and L-isomers can be separated from each other by fractional crystallization, the process provided by this invention allows one to convert the L-isomer to the preferred D-isomer.

According to the process of this invention, the bicyclic thiazolidine-azetidinone having the L-configuration or as a mixture of the L- and D-configurations is dissolved in pyridine at a temperature between about 20° C. and about 30° C. and the solution is diluted with water and is allowed to stand as the D-thiazolidine-azetidinone precipitates.

The concentration of the thiazolidine-azetidinone in the pyridine is between about 50 mg./ml. and about 10 mg./ml. The pyridine solution is diluted with water in an amount corresponding to between about 10 percent and about 50 percent by volume of pyridine. Under the conditions of temperature, concentration, and ratios of water:pyridine by volume, the D-thiazolidine-azetidinone is the least soluble of the two isomers and selectively precipitates from the epimerization mixture. When the concentration in the aqueous pyridine is too high, some L-thiazolidine-azetidinone co-precipitates with the D-form. Likewise, when the percent by volume of water is about 50 percent by volume, both the D- and L-forms can co-precipitate. Accordingly, in the process of this invention, any L-thiazolidine-azetidinone present in the epimerization mixture undergoes conversion to the D-configuration in the presence of the basic pyridine and owing to the lower solubility of the D-isomer in the aqueous pyridine it selectively precipitates while the more soluble L-configuration remains in solution for further epimerization.

Preferably, the process of this invention is carried out in pyridine containing about 15 percent by volume of water having a concentration of the thiazolidine-azetidinone of between about 50 and 75 mg. per ml.

The epimerization process of this invention is illustrated in the following reaction scheme wherein the partial structural formulas of the thiazolidine-azetidinones are used.

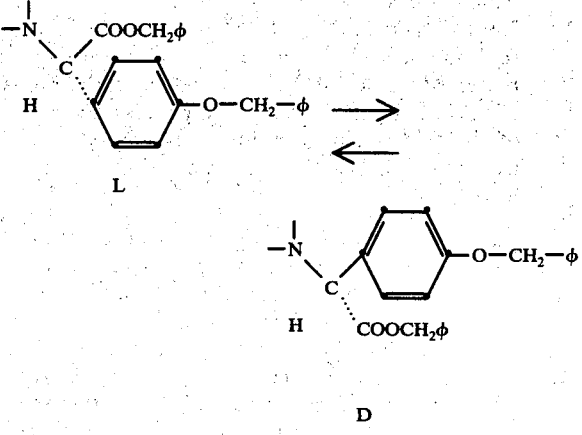

The formation of the thiazolidine-azetidinone by the base cyclization of the 5α-chlorothiazolidine amide (5) in the D-configuration is accompanied by epimerization as mentioned previously. The ratio of the D- to L-thiazolidine-azetidinone products has been determined by high pressure liquid chromatography to be about 70:30.

During the epimerization process of this invention as the least soluble D-isomer precipitates from the mixture, the ratio of D- to L- continually readjust to about 70:30 providing more D- which continues to precipitate.

As discussed above, the D-thiazolidine-azetidinone is useful in the synthesis of the antibiotic nocardicin as described in co-pending application Ser. No. 739,161 filed Nov. 5, 1976. According to the described process, the D-thiazolidine-azetidinone is reacted in an inert solvent at a temperature of about 0° to 5° C. with an oxidizing agent such as m-chloroperbenzoic acid to form the corresponding sulfoxide represented by the formula

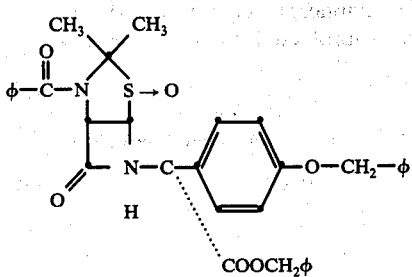

The sulfoxide is then heated in a mixture of dimethylacetamide and benzene at the reflux temperature with methanesulfonic acid to provide the thioketone substituted azetidinone represented by the formula.

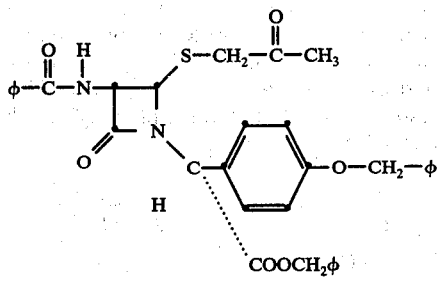

The substituted azetidinone is reacted at a temperature of about 0° C. with sulfuryl chloride and the reaction product mixture is isolated and reacted in toluene with a 3-molar excess of tri(n-butyl)tin hydride in the presence of a 3-molar excess of azobisisobutyronitrile to provide the 3-benzoylaminoazetidinone represented by the following formula.

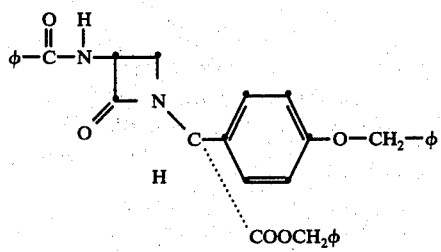

The 3-benzoylamino azetidinone ester of the above formula is deacylated to provide the corresponding 3-aminoazetidinone ester as follows. The 3-benzoylamino compound is dissolved in dry methylene chloride and excess phosphorus pentachloride is added. Pyridine is added in an amount equimolar to the PCl$_5$ and the reaction mixture is stirred at room temperature for about 30 minutes. Thereafter, the reaction is cooled to about 5° C. in an ice bath and excess dry methyl alcohol is added. The reaction mixture is stirred in the cold for about 10 minutes and thereafter is diluted with water and allowed to warm to room temperature. The 3-aminoazetidinone ester is extracted from the reaction mixture and is conveniently isolated in the form of an acid addition salt, for example, the p-toluenesulfonic acid salt or the hydrochloride salt. The free 3β-amino azetidinone ester represented by the following formula is prepared on treatment of the salt with a weak base.

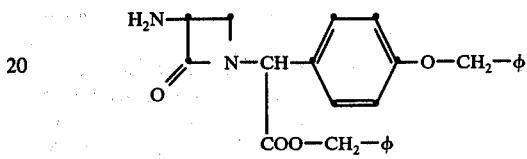

The 3-aminoazetidin-2-one represented by the above formula is an esterified and hydroxy-protected nocardicin nucleus. The nucleus is acylated with an amino-protected ester of 4-(D-3-amino-3-carboxypropoxy)-phenylglyoxylic acid O-acyloxime to provide the precursor of nocardicin, wherein the amino, hydroxy, carboxy and oximino groups are protected. The acylation is illustrated in the following reaction scheme.

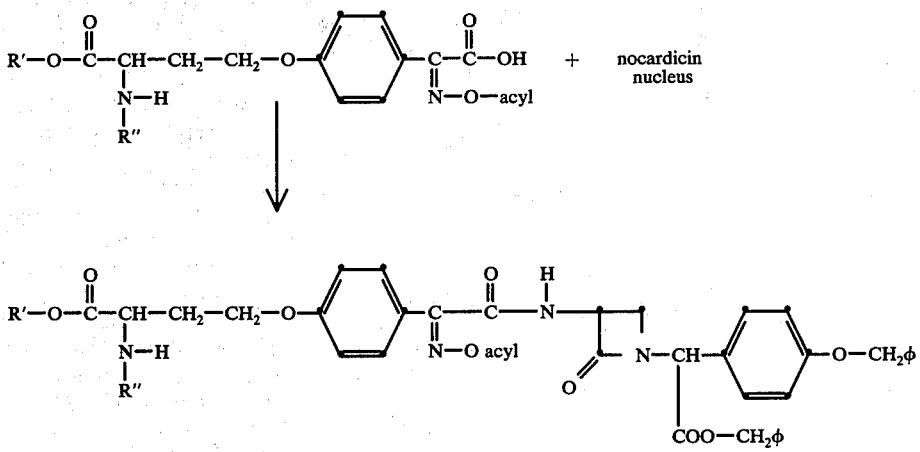

wherein R' represents a carboxylic acid-protecting group which is readily removable under acidic conditions for example, R' represents diphenylmethyl, benzyl, 4-methoxybenzyl, 2,4,6-trimethylbenzyl, or phthalimidomethyl; R" represents an amino-protecting group for example, the t-butyloxycarbonyl group and acyl represents acetyl, chloroacetyl or dichloroacetyl.

The acylation can be carried out by coupling the glyoxylic acid O-acyl oxime with the free 3β-amino nucleus compound with a condensing agent such as a carbodiimide or by forming a mixed anhydride of the glyoxylic acid O-acyl oxime and reacting the anhydride with the 3β-amino nucleus in the presence of triethylamine.

The preferred acylation method is the former wherein the acylation of the amine nucleus is carried out with the aid of a condensing agent. For example, the 3β-amino nucleus ester is reacted in an inert solvent such as methylene chloride or tetrahydrofuran with the zyl ester, with a trialkyl or triarylphosphine, and preferably triphenylphosphine, and diethyl azodicarboxylate to the amino-protected diester of the formula

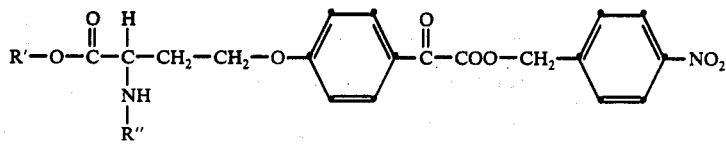

amino-protected and carboxy-protected phenylglyoxylic acid O-acyl oxime in the presence of an equimolecular amount or a small excess of a carbodiimide such as dicyclohexylcarbodiimide. The reaction mixture is maintained substantially anhydrous for best results. The reaction is carried out with stirring at about room temperature. After the reaction is complete the insoluble dicyclohexylurea is filtered and the acylation product is recovered from the filtrate.

The amino-protected and esterified phenylglyoxylic acid is prepared by the method described in co-pending application Ser. No. 739,160, filed Nov. 5, 1976. As described therein an amino-protected salt of D-methionine of the formula

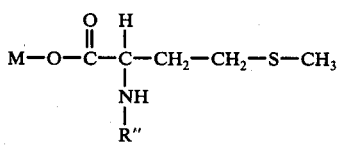

for example the salt wherein M is dicyclohexylammonium and R″ is as previously defined herein, is converted to the trimethylsilyl ester and is alkylated on the sulfur atom with an alkyl iodide or benzyl iodide, for example methyl iodide and the alkylsulfonium iodide of the formula

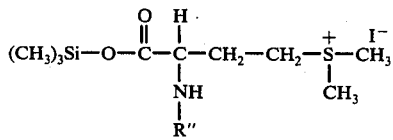

is reacted in an inert solvent with potassium t-butoxide to form the cyclic amino-protected D-homoserine lactone of the formula

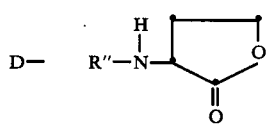

The lactone is hydrolyzed with an alkali metal hydroxide to the amino-protected D-homoserine alkali metal salt of the formula

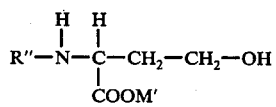

wherein M′ is sodium or potassium, and the latter is esterified e.g., with diphenylmethyl bromide. The esterified D-homoserine is then coupled with a 4-hydroxyphenylglyoxylic acid ester for example, the p-nitrobenzyl ester, with a trialkyl or triarylphosphine, and preferably triphenylphosphine, and diethyl azodicarboxylate to the amino-protected diester of the formula The p-nitrobenzyl ester group is selectively de-esterified by reduction whereby the other ester R′, which is selected from among the acid-labile ester groups, remains substantially intact. For example, the p-nitrobenzyl ester group is removed via reduction with sodium sulfide while the ester group R′ which is an acid sensitive group such as the diphenylmethyl group remains unaffected under the reduction conditions. The selective de-esterification product, the phenylglyoxylic acid, is represented by the formula

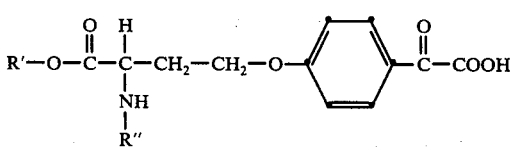

The phenylglyoxylic acid of the above formula is then converted to the oxime with hydroxylimine hydrochloride in an aqueous organic solvent mixture in the presence of a weak base such as sodium carbonate or sodium bicarbonate. The oxime is recovered from the reaction mixture by conventional procedures and is converted to the O-acyl oxime, for example, the acetyl, chloroacetyl, or dichloroacetyl derivative by reaction with the corresponding acyl chloride, for example, acetyl chloride.

Following the acylation of the nocardicin nucleus ester as described above, the nocardicin precursor (nocardicin wherein the carboxy, hydroxy, amino, and oxime functions are protected) acylation product is reacted with trifluoroacetic acid to remove the acid labile protecting groups such as the O-acyl group of the oxime; the R′ ester group, for example, the diphenylmethyl ester group; and the amino protecting group, for example, the t-butyloxycarbonylamino protecting group. The partially deblocked product is then reacted with aluminum chloride to remove the benzyl ester group and the benzyl group of the 4-benzyloxy group.

The following examples are provided to further illustrate the epimerization process of this invention.

EXAMPLE 1

A solution of 3.3 g. of a mixture D,L-2-benzoyl-3,3-dimethyl-7-oxo-α-[4-(benzyloxy)phenyl]-4-thia-2,6-diazabicyclo[3.2.0]heptane-6-acetic acid, benzyl ester (50:50 mixture of D and L by weight) in 35 ml. of pyridine was diluted with 5.25 ml. of water and allowed to stand at room temperature for 18 hours. The crystalline precipitate was filtered and washed with cold diethyl ether to yield 1.97 of the D-isomer. A second crop of the D-isomer of 0.47 g. was obtained from the filtrate and a third crop of 0.43 g. was obtained from the filtrate of the second crop.

EXAMPLE 2

To a solution of 4.1 g. of L-2-benzoyl-3,3-dimethyl-7-oxo-α-[4-(benzyloxy)phenyl]-4-thia-2,6-diazabicyclo[3.2.0]heptane-6-acetic acid, benzyl ester in 50 ml. of pyridine were added 7.5 ml. of water. The solution was stirred for about 8 hours at room temperature and the crystalline precipitate of the D-isomer was filtered. The product was dried to yield 2.45 g. and an additional 0.95 g. precipitated from the filtrate.

I claim:

1. The process for preparing in the D-configuration the compound of the formula

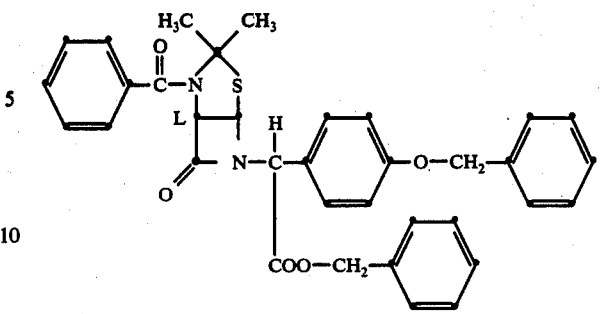

which comprises dissolving at a temperature between about 20° C. and about 30° C. said compound in the L-configuration or said compound as a mixture of the L- and D-configurations in pyridine to a concentration between about 50 mg./ml. to about 100 mg./ml.; diluting said solution with water in an amount corresponding to between about 10 percent and about 50 percent by volume; and separating said compound in the D-configuration.

2. The process of claim 1 wherein the pyridine solution is diluted with water in an amount corresponding to about 15 percent by volume.

3. The process of claim 1 wherein the compound in the L-configuration is dissolved in pyridine.

4. The process of claim 1 wherein the compound as a mixture of the D- and L-configurations is dissolved in pyridine.

* * * * *